United States Patent [19]

Mehaffy et al.

[11] 4,119,120

[45] Oct. 10, 1978

[54] FLUID SWITCH

[75] Inventors: Gordon E. Mehaffy; Kenneth B. Sawa, both of Yorba Linda, Calif.

[73] Assignee: Beckman Instruments, Inc., Fullerton, Calif.

[21] Appl. No.: 745,885

[22] Filed: Nov. 29, 1976

[51] Int. Cl.$^2$ .................... F16K 31/126; G01N 1/00
[52] U.S. Cl. .......................... 137/885; 73/422 GC; 251/61.1
[58] Field of Search ............. 137/597, 608, 525, 852, 137/853, 859, 511, 606, 607, 885; 251/335, 61.1; 73/23.1, 422 GC

[56] References Cited

U.S. PATENT DOCUMENTS

| 2,371,632 | 3/1945 | Lippincott | 92/98 R |
|---|---|---|---|
| 2,479,177 | 8/1949 | Miller | 137/606 |
| 2,677,390 | 5/1954 | Davis et al. | 251/61.1 |
| 3,186,234 | 9/1965 | Solnick et al. | 73/422 GC |
| 3,633,426 | 1/1972 | Broerman | 73/420 |

Primary Examiner—Martin P. Schwadron
Assistant Examiner—A. Michael Chambers
Attorney, Agent, or Firm—R. J. Steinmeyer; P. R. Harder; D. A. Streck

[57] ABSTRACT

Apparatus for switching a fluid stream, either gaseous or liquid, between a first path and a second path is disclosed. A pair of enclosures are formed by two depressions in a first plate (each depression having an inlet and an outlet) and an elastomeric diaphragm covering the depressions. The diaphragm is held in place by a second plate having a first control inlet opposite one depression and a second control inlet opposite the other depression. A fluid to be switched is connected into the inlets of the first plate in common. By alternately applying a control fluid to one control inlet and then the other of the second plate, the fluid to be switched is switched from one outlet to the other by the diaphragm alternately being deformed into one depression and then the other by the control fluid so as to seal the inlet and outlet and, thereby, block the flow of fluid therethrough from the inlet to the outlet. A plurality of such switching pairs are shown interconnected to provide a plurality of switching actions from a single control fluid switched source. A preferred embodiment for switching three inputs and three outputs is disclosed particularly adapted for sample loop switching in apparatus such as gas chromatographs.

3 Claims, 9 Drawing Figures (A)

(B)

(A)

(B)

(A)

(B)

FLUID SWITCH

BACKGROUND OF THE INVENTION

The present application relates to switching devices for use with fluids, either liquids or gases, and more particularly, to switching devices operated by fluid pressure.

Modern fluid sampling apparatus is designed to be accurate to a high degree. Many such devices depend upon the analysis of a discrete sample for their determination as to content. Often, accurate determination of the quantity of specific components is directly dependent upon the accuracy of the sample size. Gas chromatography is one example of such sampling and analysis apparatus wherein a fixed sample size is incorporated. To accomplish accurate sample injection into the analyzer, apparatus such as that shown in FIG. 1 is most often employed. An input for the sample gas is provided as well as an input for a carrier gas which is used to move the discrete sample into the analyzer. Appropriate valving must be provided in conjunction with a sample loop. The valving apparatus is first put in a position such as that of FIG. 1A wherein the sample gas is directed through the sample loop and thence out through a sample output. Simultaneously, the carrier gas is passed directly to the analyzer to purge out the contents of the prior analysis. When the analyzer has been purged by the carrier gas and the sample loop is full of sample gas, the valve is switched to the position of FIG. 1B. In this configuration, the sample gas is passed directly through the valve and to the sample output. At the same time, the carrier gas input is directed through the valve and into the sample loop, through the sample loop, back to the valve, and to the analyzer. As the carrier gas moves through the sample loop, the sample of gas contained therein is moved out of the sample loop and into the analyzer. The amount of sample gas moved into the analyzer, therefore, is fixed by the volume of the sample loop. Since such analyzers oftimes are used with very small samples, any leakage or lost volume in the valve contributes to inaccuracies in the readings obtained from the analyzer. Consequently, such prior art valving arrangements have commonly incorporated slider blocks or sliding cylinders such as in the apparatus of FIG. 1 wherein all connections are made into a fixed body. A slider block is mounted on the body such that when in a first position the inputs and outputs will be interconnected in one manner. When the slider block is moved into a second position, the inputs and outputs are interconnected in a different manner. In order to move the slider block between the first position and the second position, mechanical drive means as with fluid actuated pistons or such must be provided. To prevent leakage, the body and slider block assembly must incorporate various "O"-ring seals and the like. Such valves are, accordingly, large, costly, heavy, and require periodic maintenance.

Thus, it is the object of the present invention to provide an improved switching apparatus for use in the switching of fluid lines, particularly adaptable to gas sampling instruments, which is simple, light weight, can be miniaturized, and requires virtually no maintenance.

SUMMARY

The above object is achieved by providing a pair of enclosures formed by two depressions in a first plate covered by an elastomeric diaphragm. Each depression has an inlet and an outlet formed by fluid conduits passing through the plate and opening into the depressions. The two inlets are interconnected and have a common point into which a fluid to be switched can be inserted into both enclosures. The inner surface of the depressions along with the inlets and outlets therein provide a smooth surface such that the diaphragm can be deformed into the depression so as to eliminate the volume of the enclosure, seal the inlet and outlet, and prevent fluid flow from the inlet to the outlet. The diaphragm is held in place by a second plate having a first control inlet opposite one depression and a second control inlet opposite the other depression. The fluid to be switched is connected to the two interconnected inlets of the first plate. By alternately applying a control fluid to one control inlet and then the other, the fluid to be switched is switched from one outlet to the other by the diaphragm alternately being deformed into one depression and then the other by the control fluid so as to block the flow of fluid therethrough as described above. In an alternate embodiment, a plurality of such switching pairs are interconnected to provide a plurality of switching actions from a single control fluid switching source. In the preferred embodiment, three inputs and three outputs are switched simultaneously in a manner particularly adapted for sample loop switching in apparatus such as gas chromatographs.

DESCRIPTION OF THE PREFERRED EMBODIMENT

Figure 1:
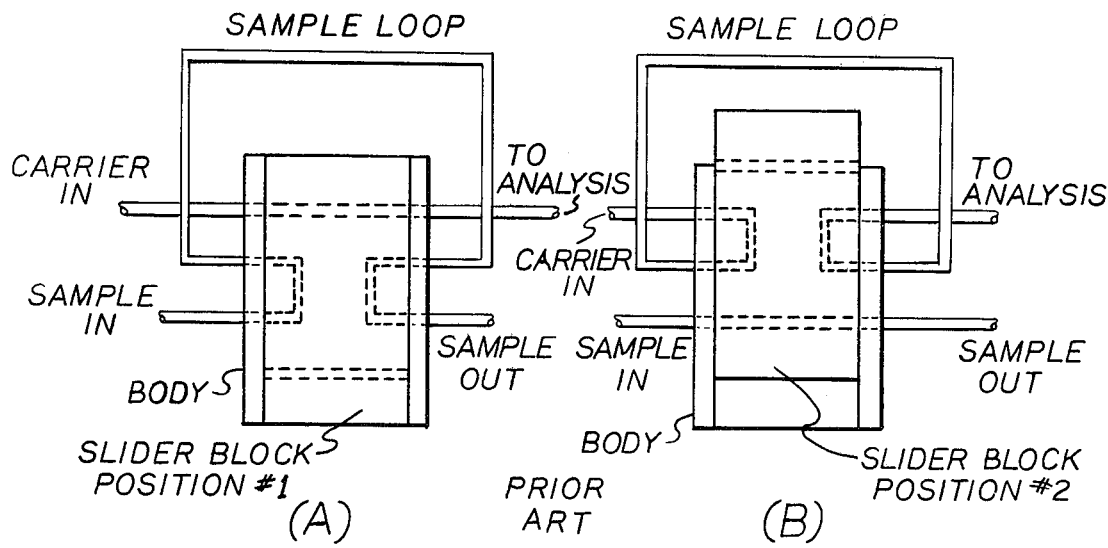
FIG. 1A and 1B is a diagram showing the operation of a two position slide valve used in the prior art for injecting a fixed volume of sample gas into a carrier gas stream for use in gas analysis apparatus such as a gas chromatograph.
Figure 2:
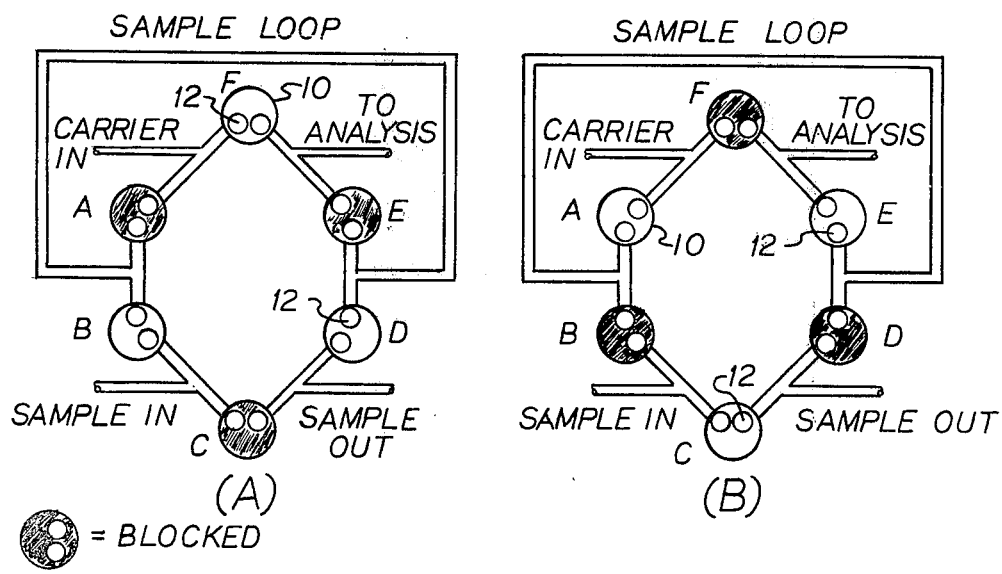
FIG. 2A and 2B is a diagram showing the operation of apparatus operating in the manner of the present invention configured to accomplish the switching functions of the two position slide valve of FIG. 1A and 1B.

As mentioned under "Background of the Invention" the present invention is directed to providing improved valving, particularly suited for applications in sample loop switching in instruments such as gas chromatographs, now accomplished by apparatus such as that shown in FIG. 1. Referring to FIG. 2, improved apparatus is shown capable of accomplishing the same functions. This improved configuration of FIG. 2 incorporates a plurality of enclosures 10, labeled A–F. Each enclosure 10 has a pair of openings 12 connected thereto adapted to be connected to a conduit. The enclosures 10 are further adapted to be "open" or "blocked" as shown by the clear or shaded symbols on the figure. In the "open" condition, fluid entering the enclosure 10 from one opening 12 is free to exit through the other opening 12. By contrast, when the enclosure 10 is in the "blocked" state, both openings 12 are sealed off and fluid can neither enter nor exit from the enclosure 10. Thus, when such an enclosure 10 is disposed in a conduit connected to the two openings 12 thereof, when the enclosure 10 is in the "open" state, the conduit will appear to be straight through, while, when the enclosure 10 is in its "blocked" state, the enclosure will appear to be closed off. Consequently, the enclosure 10 acts in the same manner as an on-off valve. With this in mind, referring to FIG. 2 with the enclosures 10 configured as shown, the apparatus of FIG. 2A functions in the same manner as that of FIG. 1A. That is, the carrier gas entering is blocked from passing through enclosure $10_A$ but is free to pass through enclosure $10_F$ and thence to the analyzer. Further passage of carrier gas is also blocked by closed enclosure $10_E$. Sample, on the other hand, enters through the sample input, passes through open enclosure $10_B$, passes through the sample loop, thence through enclosure $10_D$ and to the sample output. By blocking those enclosures 10 which were open and opening those enclosures 10 which were blocked, the apparatus as thus configured in FIG. 2B functions in the manner of the apparatus of FIG. 1B. The carrier gas enters and passes through now open enclosure $10_A$ pushing the sample gas contained in the sample loop ahead of it through now open enclosure $10_E$ to the analyzer. Sample, on the other hand, passes through open enclosure $10_c$ and directly to the sample output.

Figure 3:
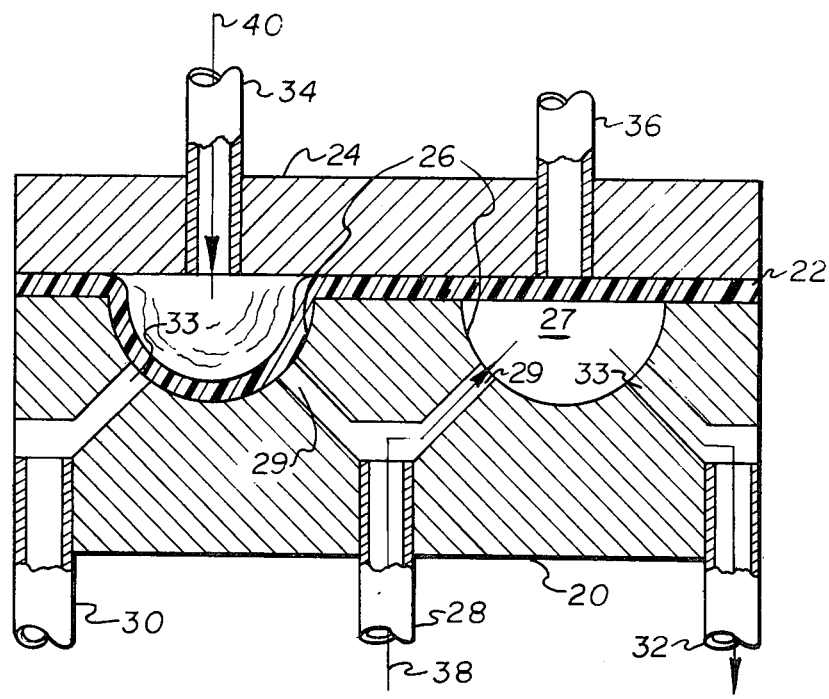
FIG. 3A and 3B is a cross-sectional drawing of the basic switching element of the present invention showing its operation to switch a single input fluid between one output line and another.
Figure 3:
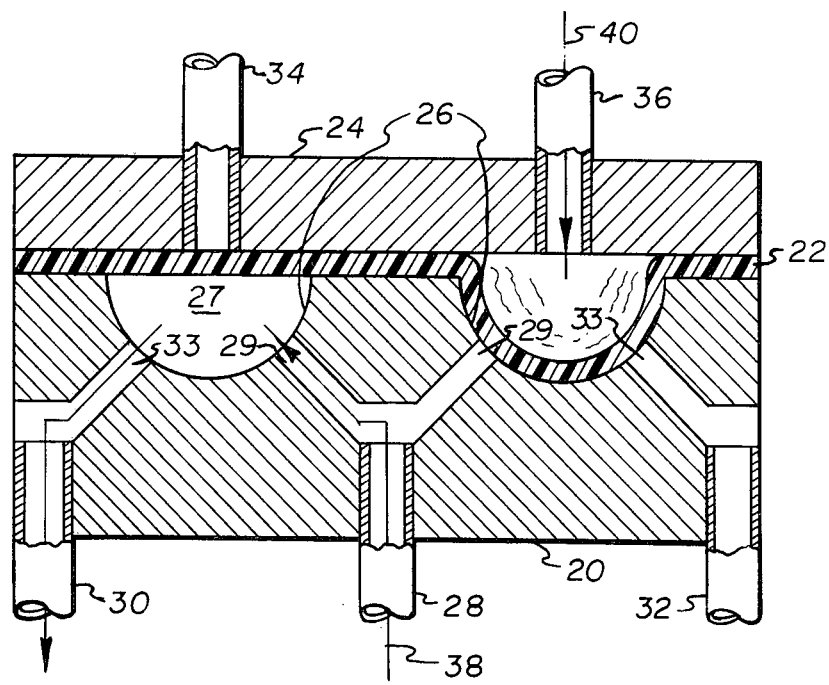

The basic switching element of the present invention is shown in FIG. 3 as comprising a tube connection plate 20, an elastomeric diaphragm 22 disposed adjacent one side of tube connection plate 20, and an actuator plate 24 disposed adjacent the other side of diaphragm 22. Tube connection plate 20 contains two depressions 26. Two enclosures 27 are thereby formed bounded by the two depressions 26 and the elastomeric diaphragm 22. An inlet conduit 28 is operably connected through tube connection plate 20 into both depressions 26 through inlet openings 29. A first outlet conduit 30 is operably connected into one depression and a second outlet conduit 32 is operably connected into the other depression through outlet openings 33. The openings 29 and 33 into the depressions 26 created for inlet conduit 28 and outlet conduits 30 and 32 are constructed, along with the interior surface of depressions 26, to present a smooth surface. A first control conduit 34 is operably connected through actuator plate 24 to open adjacent one depression 26. A second control conduit 36 is operably connected through actuator plate 24 adjacent the other depression 26. The depressions 26 are sized and the elastomeric diaphragm 22 is chosen to be of a thickness and material such that when fluid pressure is applied through one of the control conduits 34 or 36, the fluid pressure on the actuator plate 24 side of diaphragm 22 will force diaphragm 22 to deform into the adjacent depression 26 against the inner surface thereof containing openings 29 and 33 thereby sealing openings 29 and 33 into and out of the depression 26 and reducing the volume of enclosure 27 to zero.

Switching action is accomplished as shown in FIG. 3A and 3B. Referring first to FIG. 3A, a process fluid 38 under pressure $P_1$ to be switched is applied through inlet conduit 28. If a control fluid 40 under pressure $P_2$ (where $P_2$ is greater than $P_1$) is applied to first control conduit 34, the diaphragm 22 adjacent to first control conduit 34 is deformed into the adjacent depression 26 reducing the volume of enclosure 27 to zero thereby blocking the path of process fluid 38 into and through that enclosure 27. On the other hand, no pressure having been applied to second control conduit 36, process fluid 38 is free to pass into the enclosure 27 adjacent to second control conduit 36 and out into second outlet conduit 32. By removing the control fluid 40 from first control conduit 34 and applying it to second control conduit 36, in the manner of FIG. 3B, the process fluid 38 is switched to pass through the enclosure 27 adjacent first control conduit 34 and out first outlet conduit 30. Thus, process fluid 38 is switched to exit through either first outlet conduit 30 or second outlet conduit 32 depending on whether first control conduit 34 or second control conduit 36 has control fluid applied thereto. Obviously, control fluid 40 could be applied to both first control conduit 34 and second control conduit 36 to block the exit of process fluid 38 into either first outlet conduit 30 or second outlet conduit 32. In a like manner, by not applying control fluid 40 to either first control conduit 34 or second control conduit 36, process fluid 38 is free to pass into both first outlet conduit 30 and second outlet conduit 32.

Figure 4:
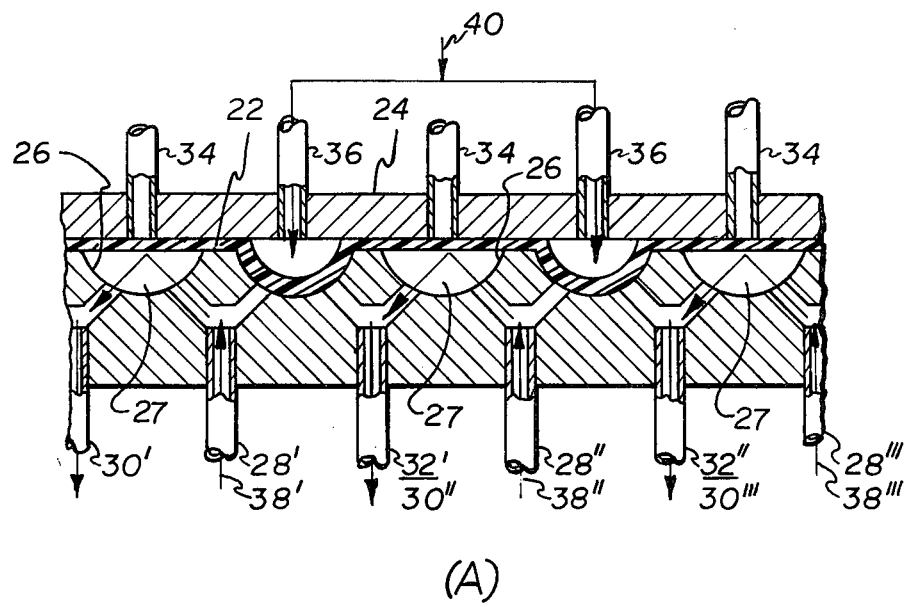
FIG. 4A and 4B is a cross-sectional drawing of a tandem switching assembly comprising a plurality of the basic switching elements of FIG. 3A and 3B.
Figure 4:
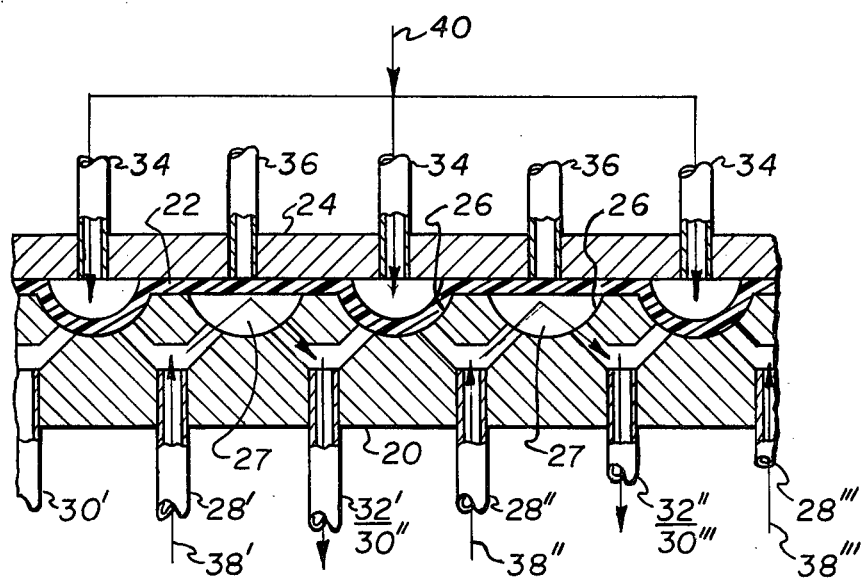

In the embodiment of FIG. 4A and B, the basic element of FIG. 3 has been incorporated into apparatus allowing a plurality of switchings to be possible under the control of a single fluid pressure source. Referring to FIG. 4A, the tube connection plate 20 now contains a plurality of depressions 26 forming a plurality of enclosures 27 in combination with diaphragm 22. Each depression 26 is connected to the depressions 26 on either side of it with a conduit adapted for external connection. As shown by the directions of the arrows thereto, the conduits in tube connector plate 20 are alternately inlet conduits and outlet conduits. For ease of correlation of FIG. 4 with FIG. 3, the inlet conduits are designated as 28', 28" and 28'''. In the same manner, the outlet conduits are designated as 30', 32'/30", and 32"/30'''. The double designation is applied to the outlet conduits since, when operating in tandem in the manner of FIG. 4, an outlet conduit is alternately fed from one inlet conduit and then from a second inlet conduit in a manner to be described in greater detail hereinafter. To operate in a tandem mode, every other depression 26 is adjacent a first control conduit 34 and the remaining depressions 26 are each adjacent a second control conduit 36. All the first control conduits 34 are connected to a common source of control fluid 40 (not shown) and all the second control conduits 36 are connected to a common alternate source of control fluid 40 (not shown). When the control fluid 40 is applied to the control conduits 36 as shown in FIG. 4A, process fluid 38' entering through inlet conduit 28' exits through outlet conduit 30'. In the same manner, process fluid 38" exits through outlet 30" and process fluid 38''' exits through outlet 30'''. By switching the control fluid 40 from control conduits 36, as shown in FIG. 4B, to control conduits 34, the process fluids are switched wherein process fluid 38' entering inlet 28' exits through outlet 32', process fluid 38" exits through outlet 32"', and process fluid 38"'' exits through another outlet conduit 32"'' (not shown).

It should be apparent, that if desired, the control conduits 34 and 36 could be actuated, by the application of control fluid thereto under pressure, individually or in various combinations to accomplish other switching and mixing actions. For purposes of the preferred embodiment as applied to gas sampling apparatus, however, the specific description is limited to switching in tandem between a first position and a second position.

Figure 5:
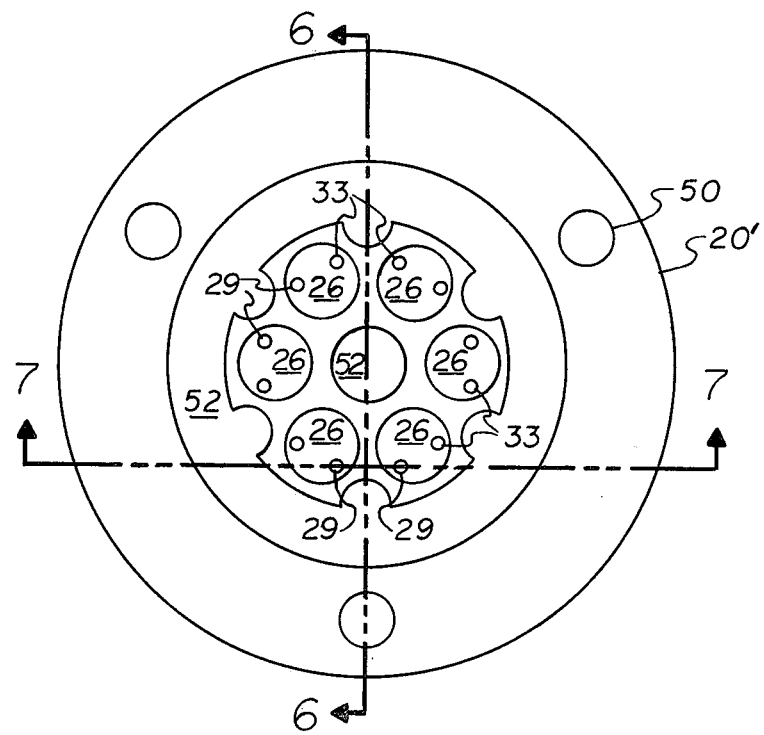
FIG. 5 is a plan view of a tube connector plate as employed in the present invention to be used in the preferred embodiment to accomplish the switching function of FIG. 2A and 2B.
Figure 6:
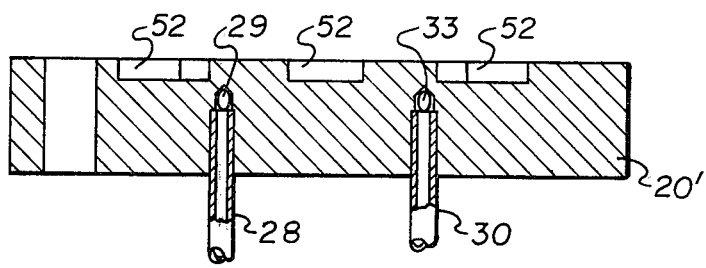
FIG. 6 is a cross-sectional drawing of the tube connector plate of FIG. 5 showing, in particular, the relief area provided for extrusion of the diaphragm in the completed assembly.
Figure 7:
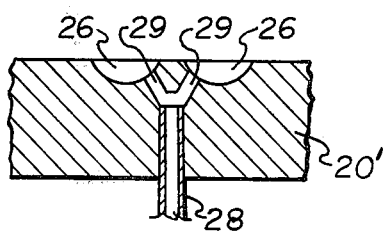
FIG. 7 is a cross-sectional drawing of one of the depressions of the tube connector plate of FIG. 5.

The preferred embodiment of the present invention is shown beginning with FIG. 5. While the closed loop construction hereinafter described contains six enclosures to allow switching of three inputs, the same principle could be applied with any even number of enclosures to allow the switching of N/2 inputs. As a practical matter, however, "useful" connections as presently envisioned are more likely with embodiments having 6, 10, or 14, etc. enclosures. As with the simple embodiments of FIGS. 3 and 4, the preferred embodiment to perform the functions of FIG. 2 comprises an elastomeric diaphragm disposed between the actuator plate 24' of FIG. 8 and the tube connector plate 20' of FIG. 5. As can be seen in FIG. 5, tube connector plate 20' contains six depressions 26 arranged in a circular closed loop pattern. Each depression 26 contains an inlet opening 29 and an outlet opening 33. The openings are arranged to be adjacent like kinds (inlet/inlet and outlet/outlet) and are interconnected between adjacent depressions 26 as shown in FIG. 7. Each interconnected inlet opening pair 29—29 has an inlet conduit 28 connected thereto as shown in FIGS. 6 and 7. Each interconnected outlet opening pair 33—33 has an outlet conduit 30 connected thereto as shown in FIG. 6. Thus, there are three inlet conduits 28 and three outlet conduits 30 which can be connected in the manner of FIG. 2. The three inlet conduits 28 are connected to "CARRIER IN", "SAMPLE IN", and the outlet of the sample loop. The three outlet conduits 30 are connected to "TO ANALYSIS", "SAMPLE OUT", and the inlet of the sample loop.

Figure 8:
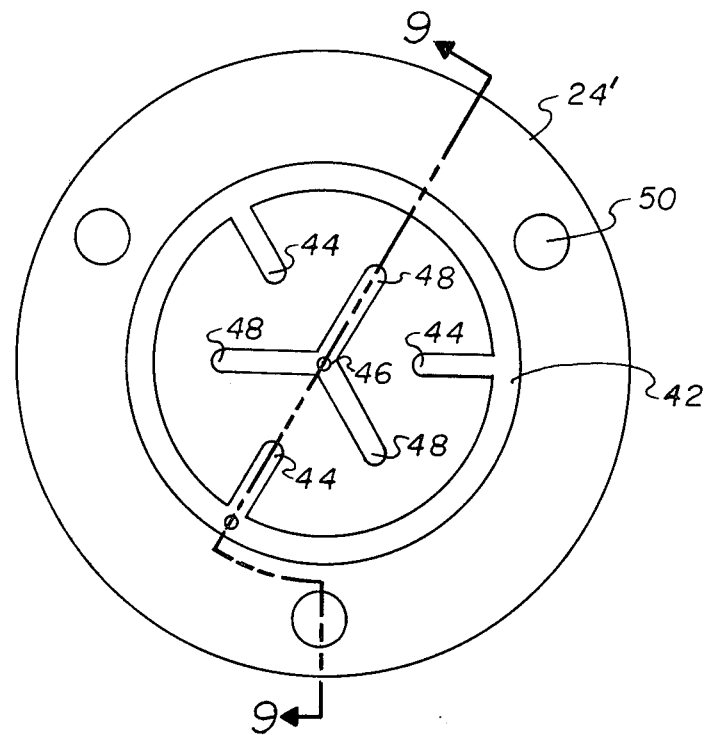
FIG. 8 is a plan view of an actuator plate to be used in conjunction with the tube connector plate of FIG. 5.
Figure 9:
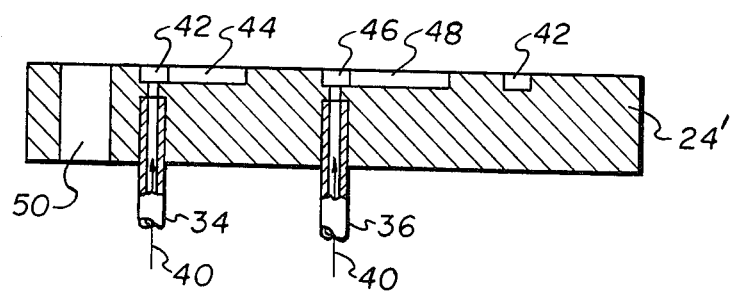
FIG. 9 is a cross-sectional drawing of the actuator plate of FIG. 8.

Referring now to FIGS. 8 and 9, the actuator plate 24' of the preferred embodiment is shown. Actuator plate 24' contains a first integral manifold channel 42 interconnecting three integral first actuation channels 44. The three first actuation channels 44 are disposed to be opposite three alternate depressions 26 when assembled with an elastomeric diaphragm between actuator plate 24' and tube connector plate 20' of FIG. 5. A first control conduit 34 is connected into first manifold channel 42. Actuator plate 24' also contains a second integral manifold channel 46 interconnecting three integral second actuation channels 48 and having a second control conduit 36 connected therein. The second actuation channels 48 are disposed to be opposite the three remaining alternate depressions 26 not opposite the first actuation channels 48 when the valve is assembled.

While the circular first manifold channel 42 and the point source second manifold channel 46 connected into "Y" connected second actuation channels 48, as shown in FIG. 8, are preferred, any of numerous configurations could be employed without departing from the spirit and intent of the present invention.

For assembly, appropriate means, such as mating holes 50 for bolts, should be provided for holding tube connector plate 20' adjacent actuator plate 24' in the proper relationship with an elastomeric diaphragm therebetween. When so assembled and with the inlet conduits 28 and outlet conduits 30 connected as described above, the switching action of the prior art valve of FIG. 1 can be accomplished by alternately applying control fluid 40 to first control conduit 34 and second control conduit 36.

Referring to FIGS. 5 and 6, when assembling the valve of FIGS. 5–9, particularly in a miniature form, it was found to be beneficial to provide the recessed area labeled 52 in tube connector plate 20' surrounding the depressions 26 to provide a non-critical area into which the elastomeric diaphragm can extrude during the assembly process or subsequent temperature expansion. By thus providing a place for excess diaphragm material to extrude, the diaphragm adjacent depressions 26 is not under a distorting force and is free to operate more correctly in the manner desired so as to open and close enclosures 27 in a reliable manner. Of course, such recessed areas could also be provided in actuator plate 24' with equal benefit.

Further, as built and tested in miniature form for incorporation in gas chromatographs manufactured by the assignee of this application, it was found to be preferable to employ a perfluoroelastomer sold under the name KALREZ by E. I. DuPont De Nemours & Co., Inc. as the diaphragm. Additionally, in the gas chromatograph application employing the KALREZ diaphragm, it was found to be preferred to employ helium as the control fluid to prevent erroneous results in the gas analysis process should any control fluid diffuse through the diaphragm material. When so constructed, the valve was able to operate in an environment of 220° C. for extended periods of time.

It is to be understood that the operation of the valve as hereinbefore described can be reversed and the terms inlet and outlet as applied can be interchanged. For example, the apparatus of FIG. 3 has been described as switching a fluid 38 entering through inlet conduit 28 between first outlet conduit 30 and second outlet conduit 32. By reversing the functions of conduits 28, 30, and 32, "outlet conduit" 28 can be supplied with a first fluid entering "first inlet conduit" 30, a second fluid entering "second inlet conduit" 32, or a mixture of both.

Having thus described our invention, we claim:

1. An improved valve for switching fluids comprising:
   (a) a first plate having a pair of depressions therein;
   (b) first and second fluid conduit means passing through said first plate and opening into respective ones of said pair of depressions;
   (c) third fluid conduit means passing through said first plate and opening into both of said pair of depressions;
   (d) a second plate assembled adjacent said first plate and having first control fluid inlet means passing through said second plate and opening opposite one of said depressions and second control fluid inlet means passing through said second plate and opening opposite the other of said depressions, each of said control fluid inlet means being connectable to a source of control fluid under pressure;
   (e) an elastomeric diaphragm disposed between said first plate and said second plate when said plates are assembled adjacent one another, said diaphragm being deformed into one of said depressions to seal said fluid conduit means opening therein when control fluid under pressure is connected to said first control fluid inlet means and being deformed into the other of said depressions to seal said fluid conduit means opening therein when control fluid under pressure is connected to said second control fluid inlet means; and, (f) means for holding said first plate, said second plate and said diaphragm in assembled adjacent relationship.

2. The improved valve of claim 1 wherein:
one of said plates contains relief areas into which said elastomeric diaphragm can flow when assembled and during temperature expansion between said first plate and said second plate whereby stresses in said diaphragm adjacent said depressions causing unreliable operation are eliminated.

3. An improved valve for controlling the input of sample to a sample analyzer comprising:

(a) a first plate having six depressions therein, each of said depressions having an inlet and an outlet; respective ones of said inlets being connected to one other of said inlets to form three interconnected inlet pairs; respective ones of said outlets being connected to one other of said outlets to form three interconnected outlet pairs;

(b) a second plate adjacent said first plate, said second plate having first control inlet means opening opposite three of said depressions and having second control inlet means opening opposite the remaining three of said depressions, said first control inlet means and said second control inlet means being individually connectable to a source of control fluid under pressure;

(c) an elastomeric diaphragm disposed between said first plate and said second plate when said plates are assembled adjacent one another, said diaphragm being deformed into said three depressions to seal the inlets and outlets thereof when control fluid is connected to said first control inlet means and being deformed into said remaining three depressions to seal the inlets and outlets thereof when control fluid is connected to said second control inlet means; and, (d) means for holding said first plate, said second plate and said diaphragm in assembled adjacent relationship.

* * * * *